(12) United States Patent
Gifford et al.

(10) Patent No.: US 10,292,384 B2
(45) Date of Patent: May 21, 2019

(54) NANOSTRUCTURES FABRICATED BY METAL ASSISTED CHEMICAL ETCHING FOR ANTIBACTERIAL APPLICATIONS

(71) Applicant: International Business Machines Corporation, Armonk, NY (US)

(72) Inventors: Stacey M. Gifford, Ridgefield, CT (US); Huan Hu, Yorktown Heights, NY (US); Pablo M. Rojas, Brooklyn, NY (US); Gustavo A. Stolovitzky, Riverdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/973,984

(22) Filed: Dec. 18, 2015

(65) Prior Publication Data
US 2017/0174848 A1   Jun. 22, 2017

(51) Int. Cl.
*B81C 1/00* (2006.01)
*B82Y 5/00* (2011.01)
(Continued)

(52) U.S. Cl.
CPC ............. *A01N 25/34* (2013.01); *A01N 59/16* (2013.01); *B81C 1/00111* (2013.01); *B81C 1/00206* (2013.01); *B81C 1/00539* (2013.01); *B81C 99/009* (2013.01); *C09K 13/08* (2013.01); *C30B 33/10* (2013.01); *B81C 1/0046* (2013.01);
(Continued)

(58) Field of Classification Search
CPC .. C08J 5/00; C08J 5/18; C08J 2300/00; B81C 99/009; B81C 1/00539; B81C 1/00206; B81C 1/0046; B81C 1/00444; B82Y 40/00; B82Y 5/00; B82Y 30/00; C09K 13/08;
(Continued)

(56) References Cited

U.S. PATENT DOCUMENTS 6,790,785 B1   9/2004  Li et al.
8,901,000 B2 * 12/2014  Braun .................... C09K 13/08
                                                    438/689
(Continued)

FOREIGN PATENT DOCUMENTS

CN        102157608 A  *  8/2011

OTHER PUBLICATIONS

Hasan, J. et al, "Selective bactericidal activity of nanopatterned superhydrophobic cicada Psaltoda claripennis wing surfaces", Applied Microbiology and Biotechnology vol. 97, 2013, pp. 9257-9262.
(Continued)

*Primary Examiner* — Anita K Alanko
(74) *Attorney, Agent, or Firm* — Cantor Colburn LLP; Vazken Alexanian

(57) ABSTRACT

The method comprises contacting a silicon substrate with a silver salt and an acid for a time effective to produce spikes having a first end disposed on the silicon substrate and a second end extending away from the silicon substrate. The spikes have a second end diameter of about 10 nm to about 200 nm, a height of about 100 nm to 10 micrometers, and a density of about 10 to 100 per square microns. The nanostructures provide antimicrobial properties and can be transferred to the surface of various materials such as polymers.

11 Claims, 8 Drawing Sheets

(51) Int. Cl.
*B81C 99/00* (2010.01)
*B82Y 30/00* (2011.01)
*B82Y 40/00* (2011.01)
*C09K 13/08* (2006.01)
*C30B 33/10* (2006.01)
*A01N 25/10* (2006.01)
*A01N 25/34* (2006.01)
*A01N 59/16* (2006.01)
*C30B 33/08* (2006.01)
*H01L 21/306* (2006.01)
*H01L 21/3213* (2006.01)

(52) U.S. Cl.
CPC ............. *B81C 1/00444* (2013.01); *B82Y 5/00* (2013.01); *B82Y 30/00* (2013.01); *B82Y 40/00* (2013.01); *C30B 33/08* (2013.01); *H01L 21/30604* (2013.01); *H01L 21/32134* (2013.01)

(58) Field of Classification Search
CPC ......... C30B 33/10; C30B 33/08; A01N 25/34; H01L 21/30604; H01L 21/32134
See application file for complete search history.

(56) References Cited

U.S. PATENT DOCUMENTS

| | | | |
|---|---|---|---|
| 8,951,430 B2 | 2/2015 | Li et al. | |
| 2008/0113283 A1* | 5/2008 | Ghoshal | B82Y 10/00 430/22 |
| 2009/0246711 A1* | 10/2009 | Kajiwara | G11B 5/855 430/320 |
| 2010/0233539 A1* | 9/2010 | Green | C09K 13/08 429/218.1 |
| 2012/0003711 A1* | 1/2012 | Tseng | B01L 3/502707 435/177 |
| 2012/0214066 A1* | 8/2012 | Miller | B82Y 30/00 429/219 |
| 2013/0211310 A1* | 8/2013 | Bommarito | B08B 17/06 602/48 |
| 2013/0338632 A1* | 12/2013 | Kaplan | A61B 17/205 604/506 |
| 2014/0021055 A1 | 1/2014 | Chiesa et al. | |
| 2015/0273755 A1* | 10/2015 | Yee | B81C 1/00206 428/206 |
| 2016/0212989 A1* | 7/2016 | Juodkazis | C12N 1/066 |

OTHER PUBLICATIONS

Hu, H. et al, "Hierarchically structured re-entrant microstructures for superhydrophobic surface with extremely low hysteresis", Journal of Micromechanics and Microengineering, vol. 24, 2014, 9 pages.

Ivanova, E. et al, "Bactericidal activity of black silicon", Nature Communications, vol. 4, 2013, 7 pages.

Ivanova, E. P. et al, "Natural Bactericidal Surfaces: Mechanical Rupture of Pseudomonas aeruginosa Cells by Cicada Wings", Small, 2012, pp. 1-6.

Li, X. et al, "Metal assisted chemical etching for high aspect ratio nanostructures: A review of characteristics and applications in photovoltaics", Current Opinion in Solid State and Materials Science, vol. 16, Issue 2, Apr. 2012, pp. 71-81.

Peng, K. et al, "Dendrite-Assisted Growth of Silicon Nanowires in Electroless Metal Deposition", Advanced Functional Materials, vol. 13. No. 2, Feb. 2003, pp. 127-132.

Sengstock, C. et al, "Structure-related anti-bacterial activity of a titanium nanostructured surface fabricated by glancing angle sputter deposition", Nanotechnology, vol. 25, 2014, 11 pages.

* cited by examiner

NANOSTRUCTURES FABRICATED BY METAL ASSISTED CHEMICAL ETCHING FOR ANTIBACTERIAL APPLICATIONS

BACKGROUND

The present disclosure relates to antimicrobial surfaces and methods of producing articles having antimicrobial surfaces, and more specifically, to nanostructures fabricated by metal assisted chemical etching for antibacterial applications.

Microorganisms are everywhere in our environment. Although many are harmless or even beneficial, some are pathogens that can cause disease or illness in human. One common route for transmission of infectious diseases is by contact with surfaces contaminated with infectious bacteria produced by an infected person. Many microbes such as viruses can survive for days on surfaces. Microbes can also grow and proliferate posing more safety and health risks.

Antimicrobial agents have been used in the past to protect surfaces from being colonized by microbes. The methods include introducing the antimicrobial agents to the surfaces to be treated via coatings. However, bacteria can develop resistance to the antimicrobial agents over time. Accordingly, alternative methods to provide an antimicrobial surface are desirable. It would be a further advantage if antimicrobial surfaces can be provided in a cost effective manner consistently on different types of materials.

SUMMARY

According to an embodiment of the present invention, a method for forming nanostructures on a silicon substrate is provided. The method comprises contacting a silicon substrate with a silver salt and an acid for a time effective to produce spikes having a first end disposed on the silicon substrate and a second end extending away from the silicon substrate. The spikes have a second end diameter of about 10 nm to about 200 nm, a height of about 100 nm to 10 micrometers, and a density of about 10 to 100 per square microns.

According to another embodiment of the present invention, a method of forming antimicrobial nanostructures on a surface of a polymer substrate comprises: providing a master template; the master template comprising a silicon substrate and a patterned surface comprising a plurality of spikes; the spikes having a first end disposed on the silicon substrate and a second end extending away from the silicon substrate; contacting a liquid material with the master template; curing the liquid material to form a patterned template; and contacting the patterned template with a polymeric material to form a polymer substrate having antimicrobial nanostructures disposed on a surface of the polymer substrate.

According to yet another embodiment of the present invention, an article comprises: a substrate having a patterned surface; the patterned surface comprising a plurality of spikes having a first end attached to the substrate and a second end extending away from the substrate; the spikes having a second end diameter of about 10 nm to about 200 nm, a height of about 100 nm to 10 micrometers, and a density of about 10 to 100 per square microns.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The following descriptions should not be considered limiting in any way. With reference to the accompanying drawings, like elements are numbered alike.

DETAILED DESCRIPTION

Methods and articles are provided that use nanostructures to control microorganisms on a surface of the articles. The surfaces have spike nanostructures and are effective to stop the growth of or eliminate various types of microorganisms.

Glancing angle deposition (GLAD) is a technique that can be used to fabricate three-dimensional nanostructures by rotating the substrate in both polar and azimuthal directions. Reactive ion etching is an etching technology used in microfabrication that uses chemically reactive plasma to remove materials deposited on wafers. Both glancing angle deposition and reactive ion etching require expensive equipment; and the fabrication processes are conducted in a vacuum environment.

Disclosed herein is a metal assisted chemical etching process that is effective to form spikes having unique structures on silicon substrates. Spikes can be made without using masks. No expensive equipment is required. The fabrication process is not conducted under vacuum and can be conveniently carried out at moderate temperatures such as room temperature and atmospheric pressure. The process is cost effective and readily scalable. The structures of the spikes are controllable by adjusting the process conditions. Advantageously the patterned surfaces have antimicrobial properties.

Moreover, methods are provided that allow the manufacture of nanostructures on materials other than silicon. The nanostructures can be formed on a hard as well as a soft surface. The articles having the nanostructure surfaces have applications in various areas such as consumer electronics, medical devices, implants, food contact applications, household products, mass transportations, and the like.

Antimicrobial nanostructures include spikes having a first end disposed on the substrate and a second end extending away from the substrate. The spikes have a second end diameter of about 10 nm to about 200 nm, a height of about 100 nm to 10 micrometers, and a density of about 10 to 100 per square microns. The spikes can also have an average spacing from about 50 nanometers to about 1 micron. The second end diameter, height, density, and average spacing are determined using microscopic technology. The density of the spikes is calculated by dividing the number of spikes on a given surface with the area of the surface.

Figure 1:
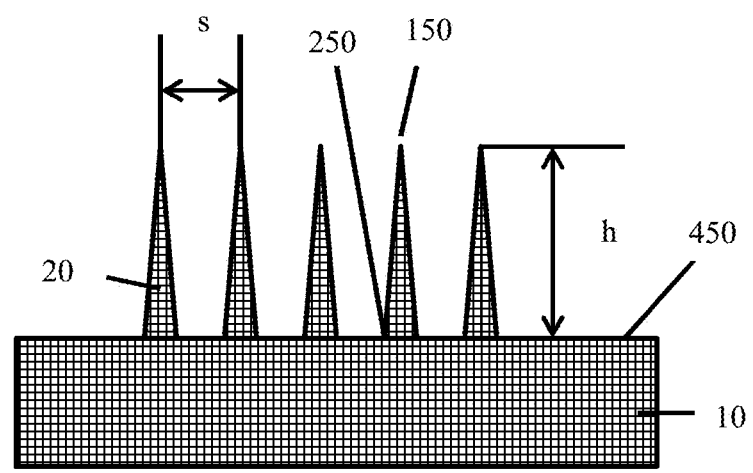
FIG. 1 illustrate antimicrobial nanostructures formed on a substrate.
Figure 2:
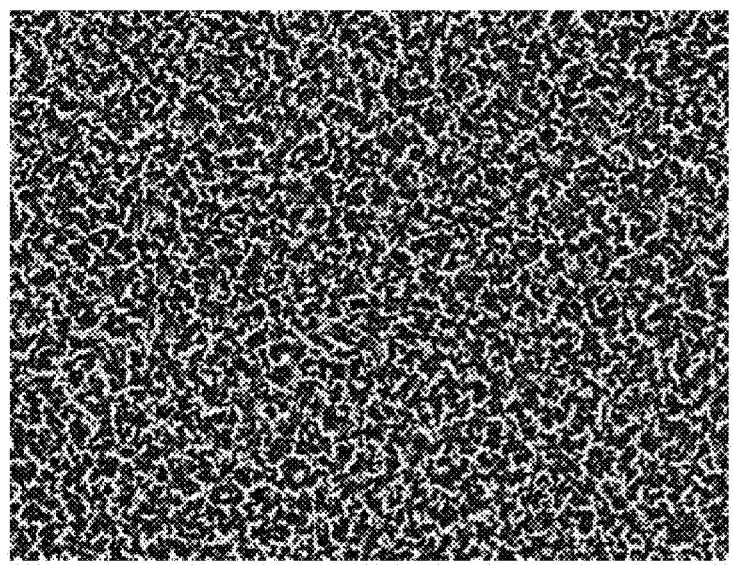
FIG. 2 is a microscopic image showing a top view of antimicrobial nanostructures according to an embodiment of the disclosure.
Figure 3:
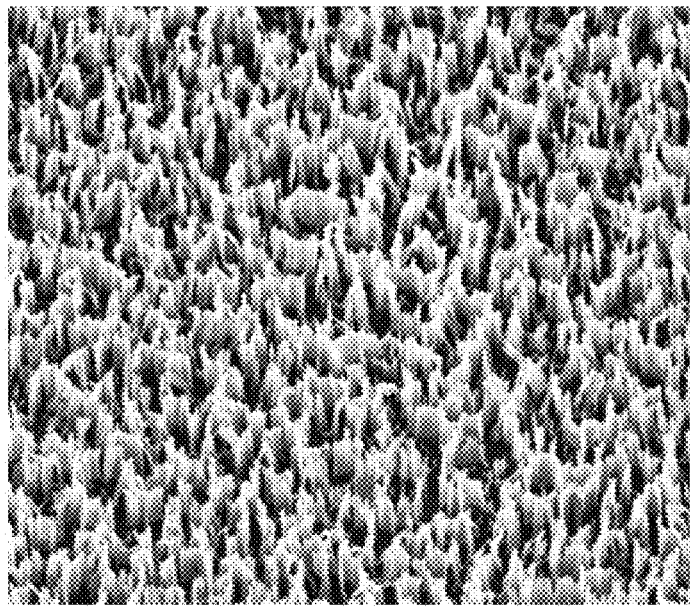
FIG. 3 is a microscopic image showing a tilted side view of antimicrobial nanostructures according to an embodiment of the disclosure.

FIG. 1 illustrates antimicrobial nanostructures formed on a substrate. The structures include spikes 20 formed on substrate 10. The spikes have a first end 250 and a second end 150. The height of the spike (h) is the distance between the second point 150 of a spike unit structure to the surface 450 of the substrate. The spacing (s) of the spikes refers to the distance between the second ends 150 of adjacent spikes 20. Although the spikes shown in FIG. 4 have tapered thickness, it is contemplated that the spikes or a portion of the spikes on a surface can have substantially uniform thickness. As used herein, "substantially uniform thickness" means that the thickness variation is less than about 10% or less than about 5%. The spike nanostructures can be formed on flat surfaces as well as on surfaces having certain shapes. Depending on the specific applications of the articles, the shapes of the antimicrobial surfaces are not particularly limited. FIG. 2 is a microscopic image showing a top view of antimicrobial nanostructures according to an embodiment of the disclosure. FIG. 3 is a microscopic image showing a tilted side view of the antimicrobial nanostructures of FIG. 2.

The spike nanostructures are effective to provide antimicrobial properties to a surface. As used herein, antimicrobial properties refer to the ability to eliminate or inhibit the growth of microorganisms. The spike nanostructures can provide antimicrobial protection covering a wide spectrum of microorganisms, e.g. bacteria, fungi, algae, yeast, mold, and the like. The bacteria include both Gram positive and Gram negative bacteria. Some examples of Gram positive bacteria include, for example, *Bacillus cereus, Micrococcus luteus*, and *Staphylococus aureus*. Some examples of Gram negative bacteria include, for example, *Escherichia coli, Enterobacter aerogenes, Enterobacter cloacae*, and *Proteus vulgaris*. Strains of yeast include, for example, *Saccharomyces cerevisiae*. Illustratively, on an unpatterned surface, microorganisms such as Gram positive bacteria *Bacillus* and Gram negative bacteria *E. Coli* replicate themselves and colonize on the surface. On a surface having spike nanostructures as defined herein, the bacteria count is significantly reduced. Without wishing to be bound by theory, it is believed that the second ends of the spikes penetrate the cell walls of the microorganisms thus eliminating or inhibiting the growth of these microorganisms.

The method of producing the nanostructures includes contacting a silicon substrate with a silver salt and an acid. The silver salt and the acid can be used sequentially or in combination. In an embodiment, the silicon substrate is contacted with an etching composition comprising a silver salt and an acid. Advantageously, the method can be conducted at a moderate temperature such as a temperature of about −10° C. to about 40° C. or about 20° C. to about 30° C.

Figure 4:
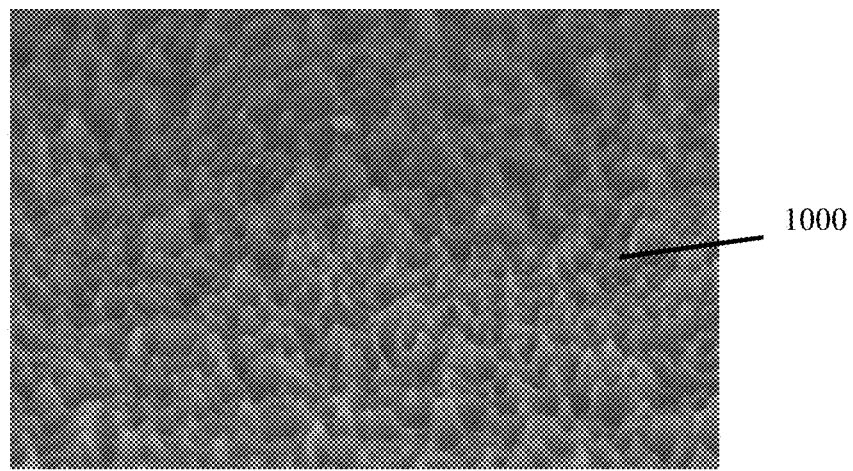
FIG. 4 is a microscopic image showing an etched silicon sample where antimicrobial structures are not formed.
Figure 5:
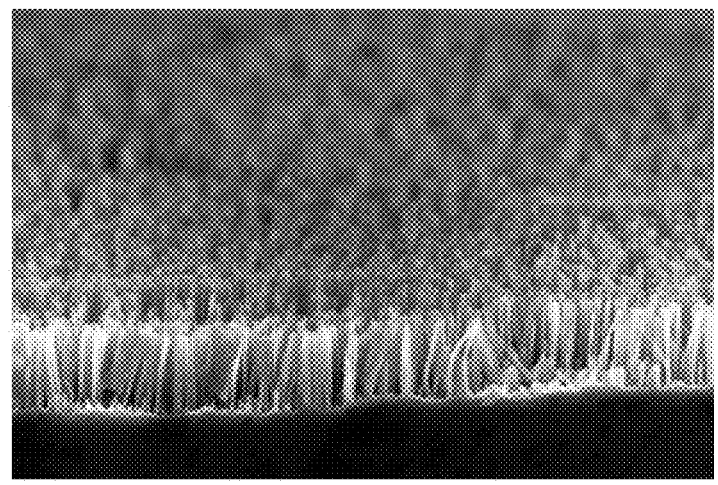
FIG. 5 is a microscopic image showing an etched silicon sample that have dense spikes.

After contacting the silver salt and the acid at an atmospheric pressure, the spike nanostructures can be produced within a few minutes. The time to etch the silicon substrate can be adjusted to control the structure of the spikes. If the etching time is too short, spikes may not be formed. FIG. 4 is a microscopic image showing an insufficiently etched silicon sample. As shown in FIG. 4, the silicon sample has island-like structures 1000 rather than spikes on its surface. Such structures may not be sharp enough to penetrate cell walls of microorganism thus they not effective to provide antimicrobial properties. If the etching time is too long, the spikes may be too dense. FIG. 5 is a microscopic image showing an overly etched silicon sample that has very dense spikes. The dense spikes have a tendency to bundle together in use thus losing their effectiveness in eliminating and inhibiting the growth of microorganisms. Depending on the specific etching composition, the etching time can vary from about 2 minutes to about 20 minutes, about 3 minutes to about 15 minutes, or about 3 minutes to about 10 minutes to produce the nanostructure as defined herein.

The silicon substrate is not particularly limited. The substrate can include silicon in amorphous or crystalline form. Although the silicon substrate can comprise metallurgical grade silicon, silicon in less pure form can also be used. In an embodiment, the silicon substrate comprises a monocrystalline silicon. Monocrystalline silicon consists of silicon in which the crystal lattice of the entire solid is continuous, unbroken to its edges, and free of grain boundaries. If desirable, before contacting the etching composition, the surface of the silicon substrate can be cleaned to remove or reduce native oxide or other impurities. Chemicals such as sulfuric acid, hydrofluoric acid, hydrogen peroxide, may be employed to clean the substrate. Other oxidant can also be used. Alternatively or in addition, the substrate may be baked in the presence of a reactive gas to clean the silicon surface.

Exemplary silver salt in the etching composition includes silver nitrate; and exemplary acid in the etching composition includes hydrofluoric acid. Other silver salts that are effective to provide silver ions can also be used. The silver salt and acid can be separately stored in aqueous solutions and mixed prior to use. Alternatively, the silicon substrate can be treated with a silver salt followed by an acid or vice versa. The concentration of the silver salt is about 1 mM to about 100 mM or about 5 mM to about 50 mM. The concentration of the acid can be about 0.1 M to about 50 M or about 1 M to about 15 M.

After nanostructures are formed, the silicon surface can be, optionally, washed or rinsed with one or more wash compositions to remove the excess etching composition and any byproducts. Useful washing compositions are not particularly limited. Exemplary washing compositions include oxidizing agents such as hydrogen peroxide. Ammonium hydroxide can also be used. In an exemplary embodiment, the etched silicon substrate is cleaned with a mixture of ammonium hydroxide and hydrogen peroxide to remove byproducts such as silver dendrite.

Silicon nanostructures can be transferred to other materials such as polymers. Some polymers are more mechanically robust than silicon. Therefore, these polymer nanostructures can be more endurable. The method of forming nanostructures on a polymer substrate includes: providing a master template, which can be a silicon substrate having spike nanostructures as disclosed herein; contacting a liquid material with the master template; curing the liquid material to form a patterned template; and contacting the patterned template with a polymeric material to form a polymer substrate having antimicrobial nanostructures disposed on a surface of the polymer substrate. Advantageously, the master mold and the patterned mold can be used repeatedly, reducing the cost and allowing the fabrication of various articles having antimicrobial surfaces.

The liquid material can be a polymer, one or more monomers, or a combination thereof. The polymer can be a thermoplastic polymer or a thermoset polymer. Exemplary polymers include epoxy, and siloxanes such as an optionally functionalized polydimethylsiloxane (PDMS). The liquid material can further contain other components such as solvents, surfactants, emulsifiers, wetting agents, curing agents, crosslinking agents, or polymerization initiators, or a combination thereof.

The curing may be a thermal cure; irradiation using ionizing or non-ionizing radiation including visible or ultraviolet light, e-beam, x-ray, or the like; chemical curing as by e.g., exposure to an active curing agent such as an acid or base; or the like. In an exemplary embodiment, the liquid material comprises an epoxy, which can be cured by UV.

Exemplary curing agents include nitrogen-containing compounds such as amines and their derivatives; oxygen-containing compounds such as carboxylic acid terminated polyesters, anhydrides, phenol-formaldehyde resins, amino-formaldehyde resins, phenol, bisphenol A and cresol novolacs, phenolic-terminated epoxy resins; sulfur-containing compounds such as polysulfides, polymercaptans; and catalytic curing agents such as tertiary amines, Lewis acids, Lewis bases; or a combination thereof. Depending on the specific liquid material used, other curing agents known in the art can also be used.

After the liquid material is cured, a patterned template is formed having surface structures that are the opposite of the surface structures on the master template. A polymeric material is then allowed to contact the patterned substrate in order to transfer the nanostructures on the surface of the master template to the surface of a polymer substrate formed from the polymeric material. In an embodiment, the contacting is conducted in a mold, and the patterned substrate is molded with the polymeric material. Molding can be conducted at room temperature or at an elevated temperature. If desired, a pressure may be applied during the molding. After the molding, the polymer substrate is released from the mold providing an article having an antimicrobial surface.

The polymeric material is not particularly limited and it can vary depending on the end use of the articles. The polymer can be a thermoset polymer, a thermoplastic polymer, or a combination thereof. The polymer substrate can be a blend of polymers, copolymers, terpolymers, or a combination thereof. The polymer substrate can also be an oligomer, a homopolymer, a copolymer, a block copolymer, an alternating block copolymer, a random polymer, a random copolymer, a random block copolymer, a graft copolymer, a star block copolymer, a dendrimer, or the like, or a combination thereof.

Illustrative examples of polymers include thermoplastic and thermosetting polymers such as polyacetals, polyolefins, polyacrylics, polyacrylates, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfonamides, polyureas, polyphosphazenes, polysilazanes, polyethylene terephthalate, polybutylene terephthalate, polyurethane, ethylene propylene diene rubber (EPR), polytetrafluoroethylene, fluorinated ethylene propylene, perfluoroalkoxyethylene, polychlorotrifluoroethylene, polyvinylidene fluoride, or the like, or a combination thereof.

Figure 6:
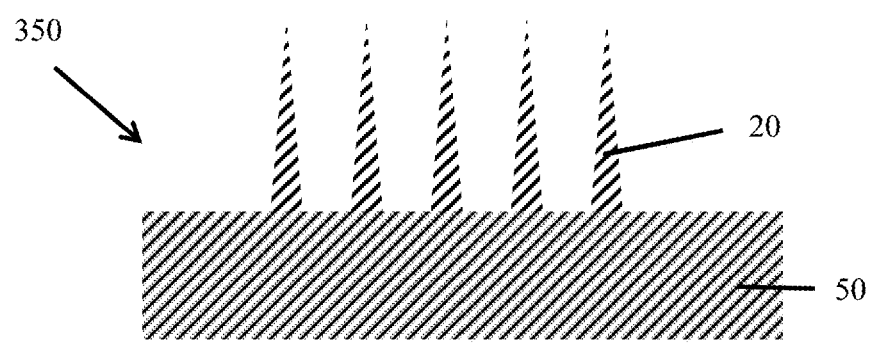
FIG. 6 illustrates a master template having a silicon substrate and spike nanostructures disposed on a surface of the silicon substrate.
Figure 7:
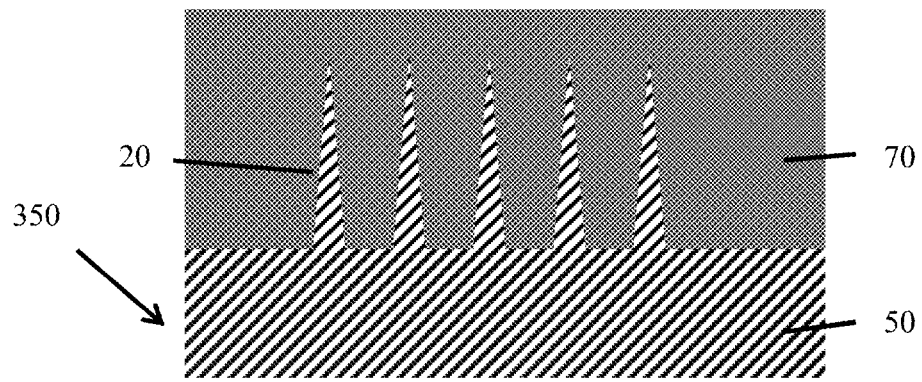
FIG. 7 illustrates the formation of a patterned template after contacting the master template of FIG. 6 with a liquid polymer material and curing the liquid polymer material.
Figure 8:
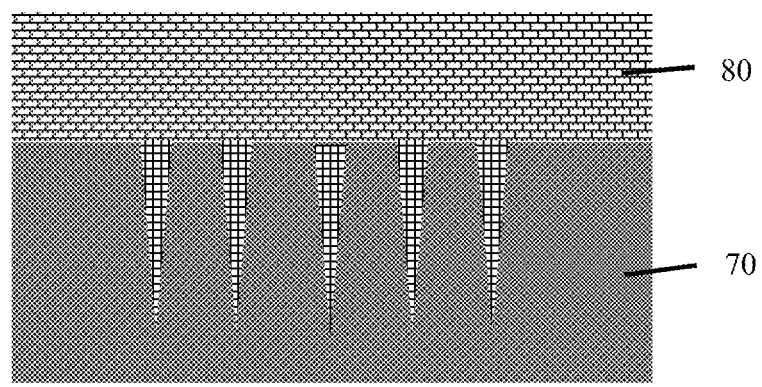
FIG. 8 illustrates the formation of a polymer substrate having an antimicrobial surface after molding the patterned template of FIG. 7 with a polymeric material.
Figure 9:
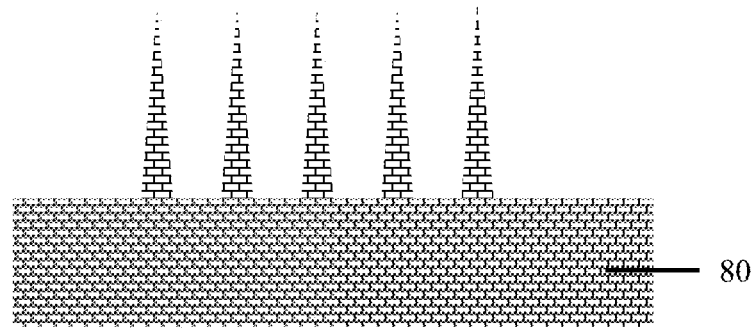
FIG. 9 illustrates the formed article having an antimicrobial surface.

A method to form articles having an antimicrobial surface is illustrated in FIGS. 6-9. FIG. 6 illustrates a master template 350 having a silicon substrate 50 and a patterned surface comprising spike nanostructures 20. FIG. 7 illustrates a patterned template 70 formed after contacting a liquid material with master template 350 and curing the liquid material. FIG. 8 illustrates the formation of a polymer substrate 80 having an antimicrobial surface after molding a polymeric material with the patterned template 70. FIG. 9 illustrates the polymer substrate 80, where the nanostructures on the surface of the polymer substrate are the same as the nanostructures on the surface of the master template 350.

The articles having an antimicrobial surface may be a simple article, an article having a complex three-dimensional structure, or may be a layer, sheet, film, or other two-dimensional surface. The articles can be a product itself or a component of a product used in consumer electronics, biodmedical products, household products, mass transportations, public buildings, food contact applications, or the like.

In an embodiment, the articles having antimicrobial surfaces are films. Such films can be used as coatings on keyboards, smartphones, laptops, or cameras.

A biomedical product can be medical devices, implants, and barrier materials. Exemplary biomedical product may include catheters, vascular grafts, blood tubings, balloons, shunts, wound dressings, surgical gowns, gloves, aprons, and drapes.

Articles having antibacterial surfaces can be used in mass transportations such as subways, buses, trains, airplanes, and ships or public buildings such as theaters, bars, and restaurants. Such articles may include components for seats, door knobs, handles, shelves, toilet seats, trays, arm rests, and the like.

Transferring the silicon spike nanostructures to polymer materials can also be used to provide flexible antibacterial fabrics. The fabrics can clean a surface as a normal cloth. In the meantime, the fabrics having the spike nanostructures can significantly eliminate bacterial on the target surface. Other household products include toys can also have this polymer materials with spike nanostructures to prevent bacterial growth.

The food grade articles include food grade containers, coffee makers, juice extractors, and blenders, or parts for coffer makers, juice extractors, and blenders.

The above embodiments are further demonstrated in the following examples, which are intended as illustrative only and are not intended to be limited thereto.

EXAMPLES

Silicon samples were cleaned using a piranha solution (a mixture of sulfuric acid and hydrogen peroxide) for 20 minutes and dipped into 1:100 diluted HF to remove native oxide. The cleaned silicon samples were dipped into a composition containing silver nitrate and HF for about 5 minutes to obtain nanostructures comprising spikes as defined herein. The silicon sample was dipped into ammonia aqueous solution to clean the patterned silicon surface.

DH5α *E. coli* cells expressing GFP or *Bacillus* were grown in LB media at 37° C. to an O.D.$_{600}$ of 1.0 (approximately $8\times10^8$ cells/mL). Cells were then diluted 1:10 and 0.5 mL of culture was incubated with patterned chips for 4 hours at 37° C. Excess media was aspirated and chips were either adhered to a 0.17 mm glass coverslip or prepared for imaging by scanning electron microscope (SEM). The number of cells was quantified per area of spikes or untreated silicon (smooth surface). The results are shown in FIGS. 10-15.

Figure 10:
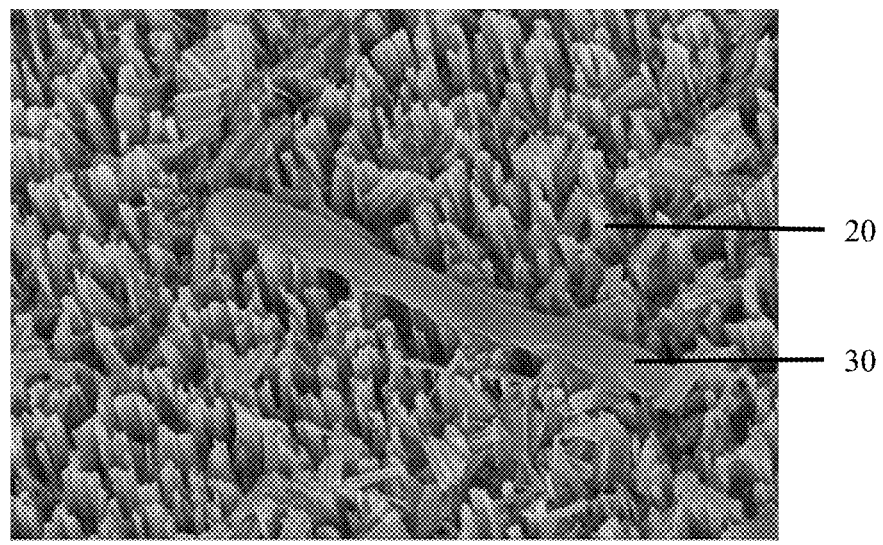
FIG. 10 is a microscopic image showing bacteria *bacillus* on a surface having antimicrobial nanostructures according to an embodiment of the disclosure.
Figure 11:
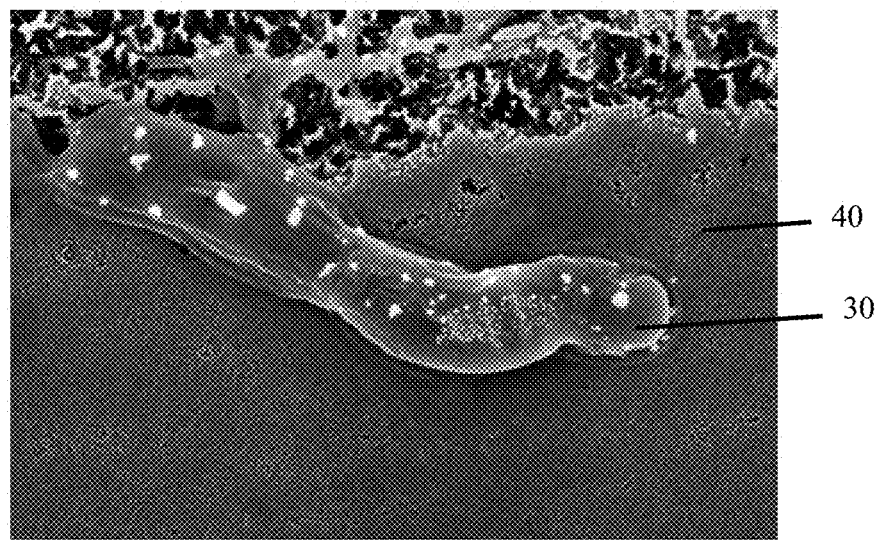
FIG. 11 is a microscopic image showing bacteria *bacillus* on a smooth surface that does not have any spikes.

FIG. 10 is a microscopic image showing bacteria *Bacillus* 30 on the silicon having patterned surface 20. FIG. 11 is a microscopic image showing bacteria *Bacillus* 30 on a smooth surface 40 that does not have any spikes. As shown in FIGS. 10 and 11, the bacterial *Bacillus* on the silicon sample having a patterned surface is thin and unhealthy whereas the *Bacillus* on the smooth surface is healthy and can grow and proliferate.

Figure 12:
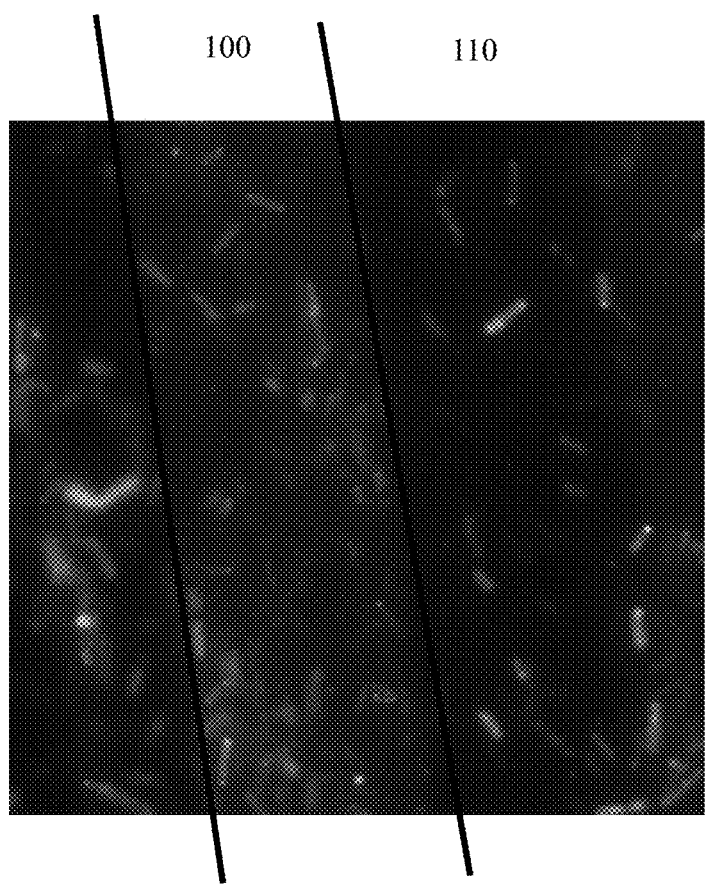
FIG. 12 is a microscopic image showing a side by side comparison of a smooth surface and a spike-containing surface treated with bacteria *E. Coli*.

FIG. 12 is a microscopic image showing a side by side comparison of a smooth surface and a spike-containing surface treated with bacteria *E. Coli*. In FIG. 12, the black area represents the substrate surface, and the white spots represent bacterial *E Coli*. As shown in the figure, the number of bacteria on the smooth surface area (100) is significantly bigger than the number of bacteria on the patterned surface area (110).

Figure 13:
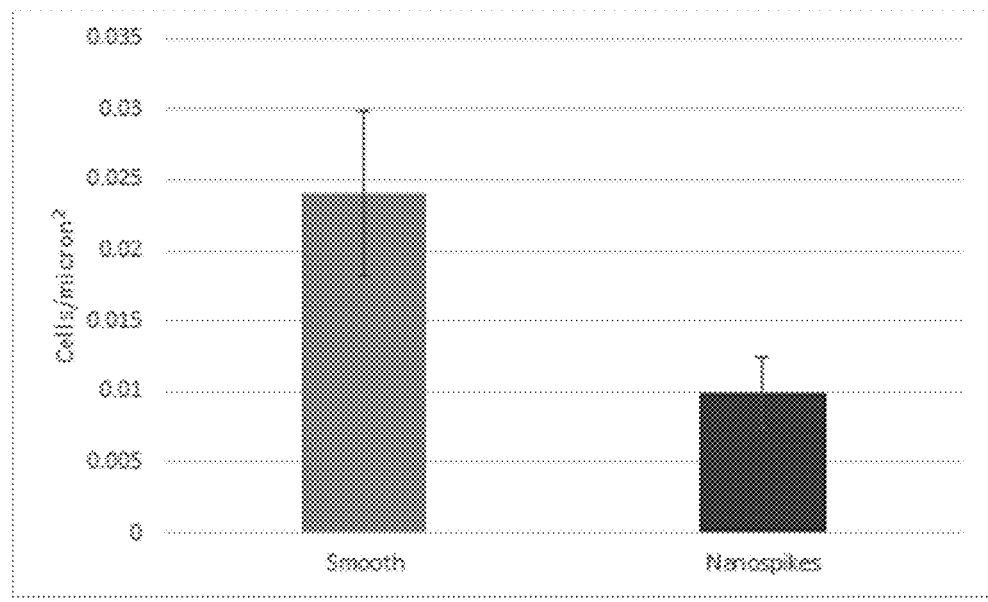
FIG. 13 is a graph comparing the bacterial *E. Coli* cell count on a smooth surface and the bacterial cell count on a spike-containing surface.

FIG. 13 is a graph comparing the *E. Coli* cell count on a smooth surface and the bacterial cell count on a spike-containing surface. The cell count on the smooth surface is at least twice as high as the cell count on a patterned surface.

Figure 14:
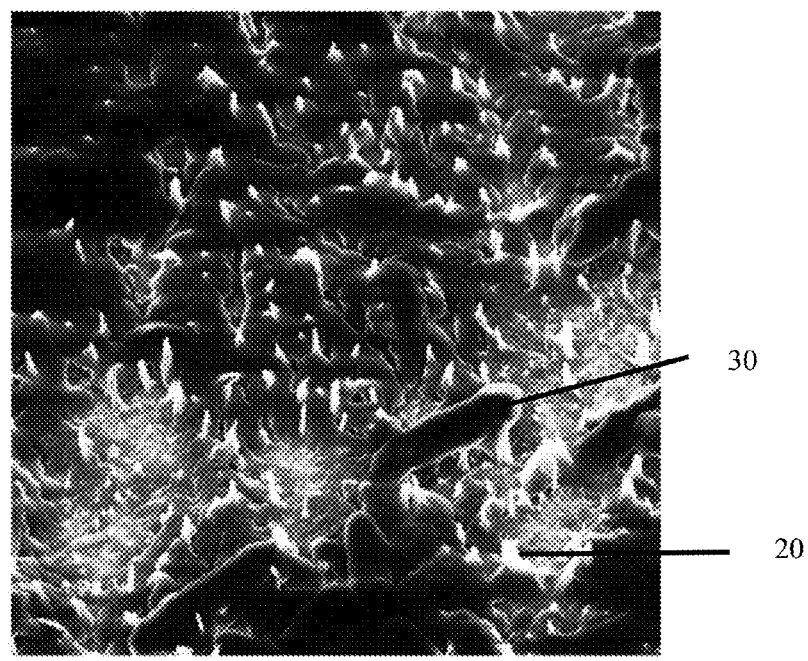
FIG. 14 is a helium microscopic image of bacteria *E. Coli* on a spike-containing surface.
Figure 15:
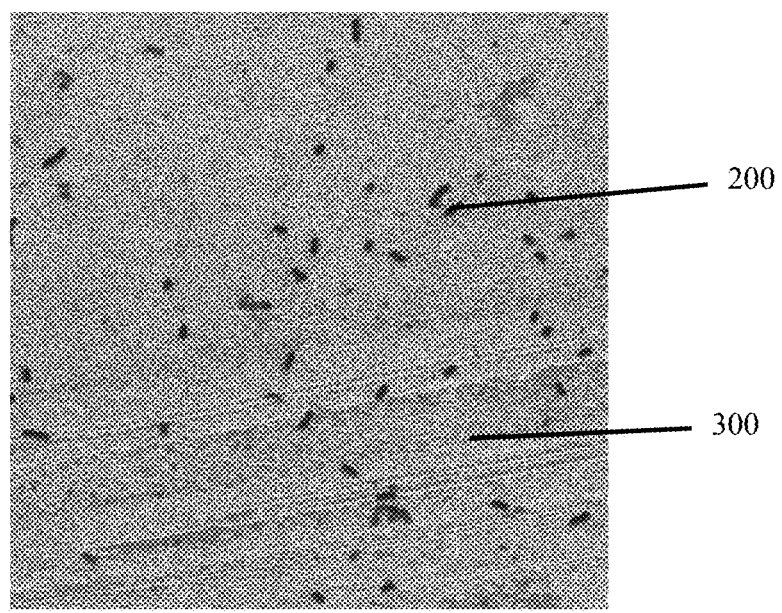
FIG. 15 is a microscopic image showing dead bacteria *E. Coli* on a spike-containing surface.

FIG. 14 is a helium microscopic image of bacteria *E. Coli* 30 on a spike-containing surface 20, and FIG. 15 is a microscopic image showing dead bacteria *E. Coli* 200 on a spike-containing surface 300.

As used herein, the terms "invention" or "present invention" are non-limiting terms and not intended to refer to any single aspect of the particular invention but encompass all possible aspects as described in the specification and claims.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method of forming antimicrobial nanostructures on a surface of a consumer electronic device, the method comprising:
    forming a master template comprising a silicon substrate having spike nanostructures by contacting a silicon substrate with a silver salt and an acid comprising hydrofluoric acid at a temperature of about 20° C. to about 30° C. for a time greater than 3 minutes to less than 10 minutes to produce spikes having a first end disposed on the silicon substrate and a second end extending away from the silicon substrate, wherein the silicon substrate comprises a monocrystalline silicon;
    the spikes having a second end diameter of about 10 nm to about 200 nm, a height of about 100 nm to about 1 micrometer, and a density of about 10 to 100 per square microns, wherein the concentration of the silver salt is about 5 mM to 9 mM and the concentration of the acid is about 1 M to about 15 M;
    contacting a liquid material with the master template, wherein the liquid material comprises a thermoplastic polymer;
    curing the liquid material to form a patterned template, wherein the curing comprises radiation curing;
    contacting the patterned template with a polymeric material to form a polymer film having antimicrobial nanostructures on a surface of the polymer film; and
    applying the polymer film as a coating to the surface of the consumer electronic device;
    wherein the antimicrobial structures on the surface of the polymer film comprise a plurality of spikes that are the same as the spikes on the silicon substrate; and
    wherein the antimicrobial structures on the surface of the polymer film eliminate microorganisms or inhibit the growth of microorganisms.

2. The method of claim 1, wherein the polymeric material comprises polyacetals, polyolefins, polyacrylics, polyacrylates, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfonamides, polyureas, polyphosphazenes, polysilazanes, polyethylene terephthalate, polybutylene terephthalate, polyurethane, ethylene propylene diene rubber, polytetrafluoroethylene, fluorinated ethylene propylene, perfluoroalkoxyethylene, polychlorotrifluoroethylene, polyvinylidene fluoride, or the like, or a combination thereof.

3. The method of claim 1, wherein the silver salt comprises silver nitrate.

4. The method of claim 1, wherein the microorganisms comprise bacteria, fungi, algae, yeast, mold, or a combination thereof.

5. The method of claim 1, wherein the second end of the spikes is effective to penetrate a cell wall of the microorganisms.

6. The method of claim 1, wherein the microorganisms comprise bacteria *Bacillus*, bacteria *E. Coli*, or a combination thereof.

7. The method of claim 1, wherein an average spacing between second ends of adjacent spikes is about 50 nanometers to about 1 micron.

8. The method of claim 1, wherein the spikes have tapered thickness.

9. The method of claim 1, wherein the spikes has a thickness variation of less than about 10%.

10. The method of claim 1, wherein the consumer electronic device comprises a keyboard, smartphone, laptop, or camera.

11. A method of forming antimicrobial nanostructures, the method comprising:
    forming a master template comprising a silicon substrate having spike nanostructures by contacting a silicon substrate with a silver salt and an acid comprising hydrofluoric acid at a temperature of about 20° C. to about 30° C. for a time greater than 3 minutes to less than 10 minutes to produce spikes having a first end disposed on the silicon substrate and a second end extending away from the silicon substrate, wherein the silicon substrate comprises a monocrystalline silicon;

the spikes having a second end diameter of about 10 nm to about 200 nm, a height of about 100 nm to about 1 micrometer, and a density of about 10 to 100 per square microns, wherein the concentration of the silver salt is about 5 mM to 9 mM and the concentration of the acid is about 1 M to about 15 M;

contacting a liquid material with the master template, wherein the liquid material comprises a thermoplastic polymer;

curing the liquid material to form a patterned template, wherein the curing comprises radiation curing;

contacting the patterned template with a polymeric material to form a polymer film having antimicrobial nanostructures on a surface of the polymer film; and applying the polymer film as a coating to the surface of a seat, door knob, handle, shelve, toilet seat, tray, or arm rest;

wherein the antimicrobial structures on the surface of the polymer film comprise a plurality of spikes that are the same as the spikes on the silicon substrate; and wherein the antimicrobial structures on the surface of the polymer film eliminate microorganisms or inhibit the growth of microorganisms.

* * * * *